US006804561B2

(12) United States Patent
Stover

(10) Patent No.: US 6,804,561 B2
(45) Date of Patent: Oct. 12, 2004

(54) ANTENNA FOR MINIATURE IMPLANTED MEDICAL DEVICE

(75) Inventor: Howard H. Stover, Pasadena, CA (US)

(73) Assignee: Alfred E. Mann Foundation for Scientific Research, Santa Clarita, CA (US)

( * ) Notice: Subject to any disclaimer, the term of this patent is extended or adjusted under 35 U.S.C. 154(b) by 511 days.

(21) Appl. No.: 09/967,737

(22) Filed: Sep. 28, 2001

(65) Prior Publication Data

US 2002/0042637 A1 Apr. 11, 2002

Related U.S. Application Data

(60) Provisional application No. 60/239,289, filed on Oct. 11, 2000.

(51) Int. Cl.[7] .............................................. A61N 1/375
(52) U.S. Cl. ...................................................... 607/60
(58) Field of Search ............................. 607/30, 32, 36, 607/55–57, 59–60; 128/903; 600/302

(56) References Cited

U.S. PATENT DOCUMENTS

| | | | |
|---|---|---|---|
| 3,713,162 A | 1/1973 | Munson et al. | |
| 4,524,774 A | 6/1985 | Hildebrandt | |
| 5,193,539 A | 3/1993 | Schulman et al. | |
| 5,193,540 A | 3/1993 | Schulman et al. | |
| 5,312,439 A | 5/1994 | Loeb | |
| 5,324,316 A | 6/1994 | Schulman et al. | |
| 5,405,367 A | 4/1995 | Schulman et al. | |
| 5,406,297 A | 4/1995 | Caswell et al. | |
| 5,626,630 A | * 5/1997 | Markowitz et al. | ......... 607/760 |
| 6,163,305 A | 12/2000 | Murakami et al. | |
| 6,164,284 A | 12/2000 | Schulman et al. | |
| 6,185,452 B1 | 2/2001 | Schulman et al. | |
| 6,208,894 B1 | 3/2001 | Schulman et al. | |
| 6,218,994 B1 | 4/2001 | Mileski et al. | |
| 6,218,995 B1 | 4/2001 | Higgins et al. | |
| 6,229,494 B1 | 5/2001 | Merenda | |
| 6,266,567 B1 | * 7/2001 | Ishikawa et al. | .............. 607/36 |
| 6,315,721 B2 | 11/2001 | Schulman et al. | |
| 6,415,184 B1 | * 7/2002 | Ishikawa et al. | .............. 607/45 |
| 6,482,154 B1 | * 11/2002 | Haubrich et al. | ........... 600/300 |
| 2001/0001125 A1 | 5/2001 | Schulman et al. | |

* cited by examiner

*Primary Examiner*—Kennedy Schaetzle
*Assistant Examiner*—Kristen Droesch
(74) *Attorney, Agent, or Firm*—Lee J. Mandell

(57) ABSTRACT

An improved antenna for use with an implantable microdevice, such as a microstimulator or microsensor, comprises a loop antenna on the case of the microdevice. The antenna receives data transmitted from an external device, and transmits data to an external device. Such a loop antenna may be formed from two cylindrical sections separated by an insulating material on the case of the microdevice, or by separating a metal cylinder into two parallel semi-cylinders separated by an insulating material. A tuning circuit comprising capacitors and/or varactors is used to obtain resonance in the loop antenna, thus creating a sufficiently large effective antenna aperture. In a preferred embodiment, the electrodes of the microdevice are modified to both perform their primary task of tissue stimulation and to perform a secondary task as the radiating elements of a loop antenna.

38 Claims, 4 Drawing Sheets

ANTENNA FOR MINIATURE IMPLANTED MEDICAL DEVICE

This application claims the benefit of U.S. Provisional Application No. 60/239,289, filed Oct. 11, 2000.

BACKGROUND OF THE INVENTION

The present invention relates to implantable medical devices, and more particularly to implantable micro stimulators or sensors, hereafter referred to as microstimulators or microsensors. Such devices have electrodes attached to muscle or nerve fibers, through which the devices electrically stimulate the muscle or nerve fibers, or sense one or more physiological states present in the muscle or nerve fibers. More particularly, the invention relates to an improved antenna for such implantable microdevices, for both receiving signals from an external device, and transmitting signals to an external device.

Neurological disorders are often caused by neural impulses failing to reach their natural destination in otherwise functional body systems. Local nerves and muscles may function, but, for various reasons, injury, stroke, or other cause, the stimulating signals do not reach their natural destination.

For example, paraplegics and quadriplegics have intact muscles and only lack the complete brain-to-muscle nerve link which conducts the signal to the muscles.

Prosthetic devices have been used for some time to provide electrical stimulation to excite muscle, nerve or other cells to provide relief from paralysis, and various other physical disorders have been identified which may be treated by electrical stimulation devices. Some of these devices have been large bulky systems providing electrical pulses through conductors extending through the skin. Disadvantageously, complications, including the possibility of infection, arise in the use of stimulators which have conductors extending through the skin.

Other smaller stimulators have been developed that are fully implantable and are controlled through high-frequency, modulated RF, telemetry signals. Such systems designed to stimulate nerves or muscles to provide motion are know as Functional Electrical Stimulation (FES) systems. An FES system using telemetry signals is set forth in U.S. Pat. No. 4,524,774, issued Jun. 25, 1985 for "Apparatus and Method for the Stimulation of a Human Muscle." The '774 patent teaches a source of electrical energy, modulated in accordance with desired control information, to selectively power and control numerous, small stimulators, disposed at various locations within the body. Thus, for example, a desired progressive muscular motion may be achieved through the successive or simultaneous stimulation of numerous stimulators, directed by a single source of information and energy outside the body.

Many difficulties arise in designing implanted stimulators which are small in size, and in passing sufficient energy and control information to the stimulators to satisfactorily operate them without direct connection. A design of a small functionally suitable stimulator, a microstimulator, is taught is U.S. Pat. No. 5,324,316 issued Jun. 28, 1994 for "Implantable Microstimulator." The '316 patent teaches all the elements required for successful construction and operation of a microstimulator. The microstimulator is capable of receiving and storing sufficient energy to provide the desired stimulating pulses, and also is able to respond to received control information defining pulse duration, current amplitude and shape. The microstimulator of the '316 patent can also be easily implanted, such as by expulsion through a hypodermic needle. The '316 patent is incorporated herein by reference.

Known microstimulators utilize a telemetry receiver based on modulating an inductive power signal provided to the microstimulator. Similarly, signals are back transmitted from the microstimulator using the same circuits. By using components already present in the microstimulator, these telemetry systems do not require substantial additional circuitry. However, such inductive telemetry methods are limited by the resonant frequencies of the existing coil, which are typically below 2 MHz. While this approach has proven adequate for many applications, there are potential problems with interfering signals. Further, much higher frequencies, 402 MHz to 405 MHz, have been designated by the Federal Communications Commission (FCC) for use with medical devices.

Telemetry methods utilizing monopole and dipole antennas are known for use in the FCC designated frequency range, however, such antennas are, primarily, electrical field devices. Electrical field devices suffer from high tissue detuning (i.e., the surrounding tissue interacts with the electrical nature of circuit components to the extent that some effectiveness of tuning is lost) and may not provide the best performance for implantable devices. Other telemetry systems utilizing a loop antenna inside the microdevice are also known in the art. Loop antennas have the advantage of being magnetic field devices, and are therefore less susceptible to tissue detuning. However, placing the loop antenna inside the case of a microdevice exhausts scarce space within the microdevices.

What is needed is a telemetry system, suitable for operation in the 402 MHz to 405 MHz frequency range, that does not suffer from high tissue detuning loss, and that does not take up substantial space within the implantable microdevice.

SUMMARY OF THE INVENTION

The present invention addresses the above and other needs by providing a loop antenna formed on the case of an implantable microdevice. The improved antenna receives data transmitted from an external device, and transmits data to an external device. Such a loop antenna may be formed from two cylindrical sections separated by an insulating material on the case of the microdevice, or by separating a metal cylinder into two parallel semi-cylinders separated by an insulating material. A tuning circuit comprising capacitors and/or varactors is used to obtain resonance in the loop antenna, thus creating a sufficiently large effective antenna aperture. Advantageously, such a loop antenna is suitable for operation in the 402 MHz to 405 MHz frequency range, is a magnetic field device and therefore not susceptible to high absorption losses, and does not require space in the interior of the microdevice.

In accordance with one aspect of the invention, a loop antenna is formed on the case of an implantable microdevice. By forming the antenna on the case, space inside the microdevice is available for circuit components. In one embodiment of the invention, the existing electrodes, on the case of a microstimulator, are combined with a reactive circuit to create a loop antenna.

It is a feature of the invention to provide an implantable medical device having a loop antenna, which loop antenna is advantageously a magnetic field device. Magnetic field devices are less prone to degradation from tissue absorption than are electrical field devices, such as dipole and monopole antennas. Accordingly, once implanted, a magnetic field device is more stable and predictable than an electrical field device.

In accordance with another aspect of the invention, a loop antenna provided in an implantable medical device may be tuned with an array of capacitors and/or varactors. Because of the small physical size of the antenna, the antenna is not an effective radiator at the targeted operating frequencies without tuning. Accordingly, the capacitance provided by an array of capacitors and/or varactors is adjusted to be equal to the inductive reactance of the loop, resulting in a high Q circuit and a larger effective antenna size.

In accordance with yet another aspect of the invention, a telemetry system using a loop antenna provides non-inductive telemetry capability. Inductive telemetry requires that the transmitter and receiver be in very close proximity for effective operation. The telemetry system provided by the loop antenna does not include such limitations.

BRIEF DESCRIPTION OF THE DRAWINGS

The above and other aspects, features and advantages of the present invention will be more apparent from the following more particular description thereof, presented in conjunction with the following drawings wherein.

Corresponding reference characters indicate corresponding components throughout the several views of the drawings.

DETAILED DESCRIPTION OF THE PREFERRED EMBODIMENTS

The following description is of the best mode presently contemplated for carrying out the invention. This description is not to be taken in a limiting sense, but is made merely for the purpose of describing the general principles of the invention. The scope of the invention should be determined with reference to the claims.

Figure 1:
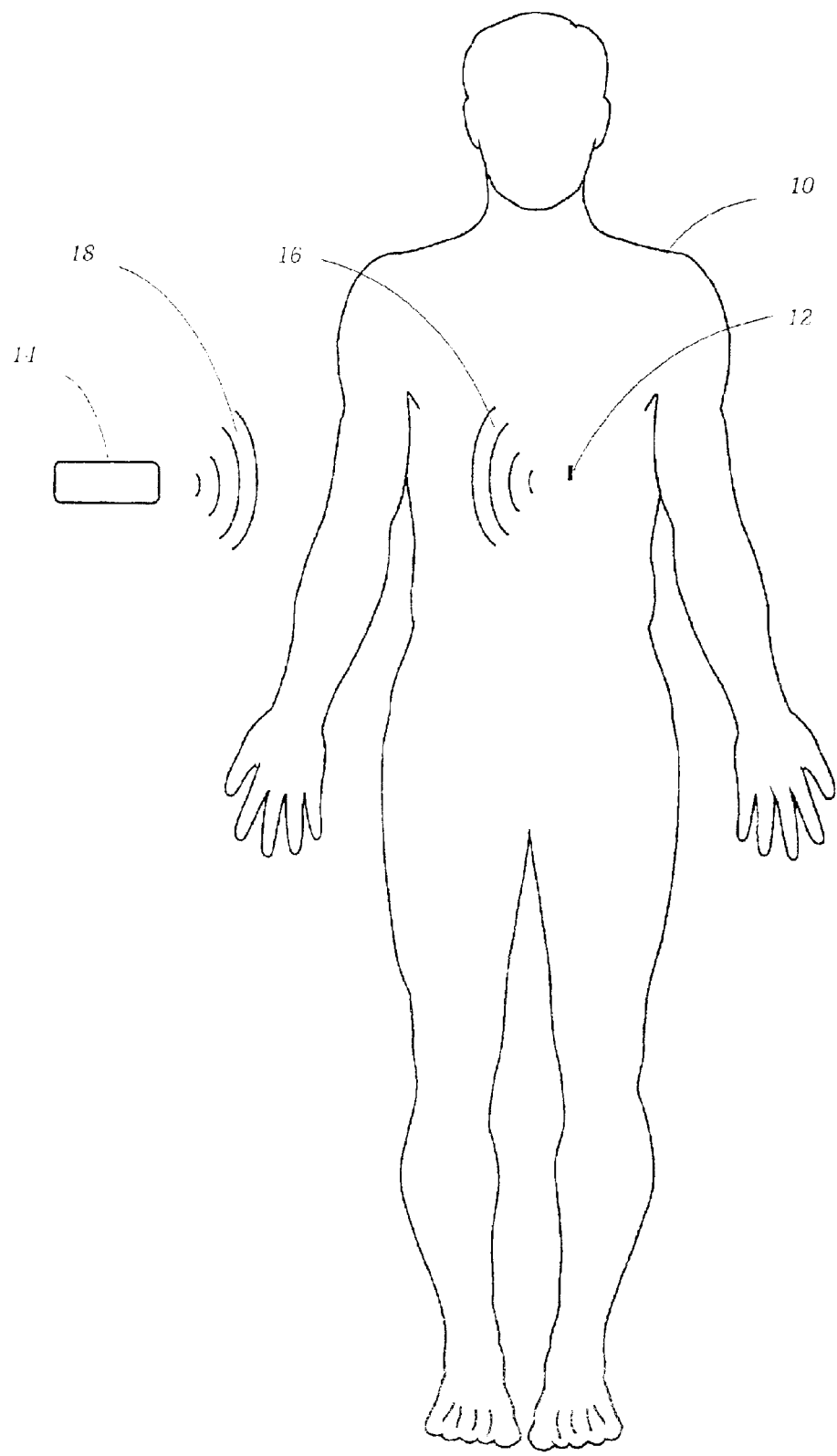
FIG. 1 shows a patient with an implanted microdevice and an external device adapted to be in telecommunicative contact with the implanted microdevice.

As seen in FIG. 1, the present invention applies to a microdevice 12 implanted in a patient 10. An external device 14 transmits signals, represented in FIG. 1 by the arced lines 18, to the microdevice 12 and the microdevice 12 transmits signals, represented by the arced lines 16, to the external device 14. The signals 18 transmitted to the microdevice 12 are principally control signals. The signals 16 transmitted from the microdevice 12 may be status signals, including diagnostic signals and/or performance signals (e.g., battery voltage), or signals that represent sensed physiological values. Those skilled in the art will appreciate that signals used for other purposes may also be transmitted from an implanted device, and the transmission of those signals using a loop antenna formed on the case of an implantable device falls within the scope of the present invention.

Figure 2A:
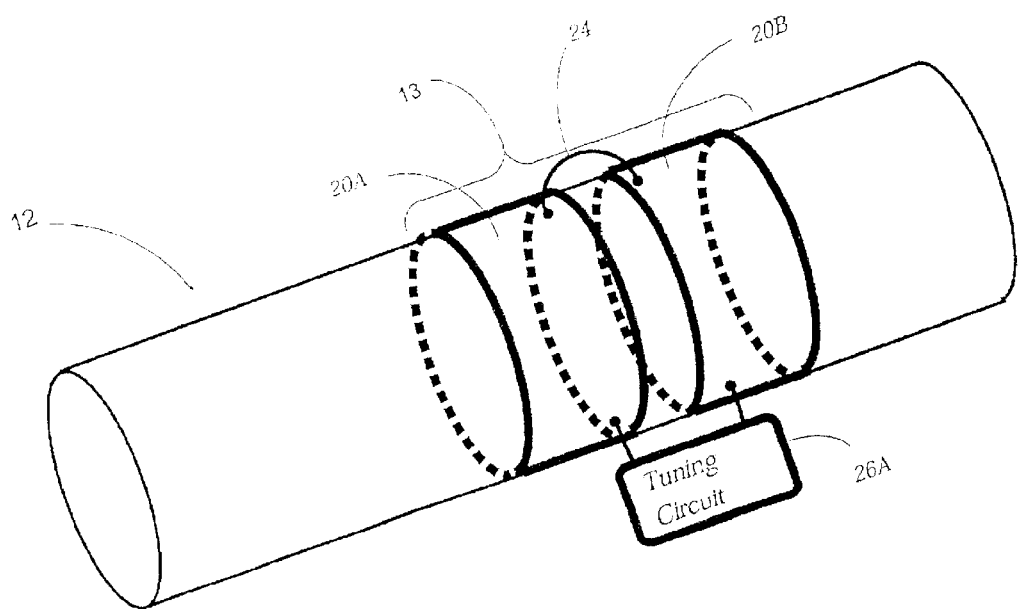
FIG. 2A depicts a first embodiment of a loop antenna formed on the case of an implantable microdevice.

The present invention pertains to a loop antenna 13 formed on the case of the microdevice 12. Such a loop antenna 13 is shown in FIG. 2A in the form of two cylindrical sleeves 20A and 20B. The cylindrical sleeves 20A and 20B form the radiating element of the loop antenna. The cylindrical sleeves 20A and 20B are separated either by a gap or by an insulating material.

A tuning element is typically required to increase the effective aperture of a loop antenna. The tuning element is reactively matched to the radiating element to create a resonant circuit. A tuning element comprising a tuning circuit 26A and a short 24 is shown in FIG. 2A. The tuning circuit 26A is electrically connected between the cylindrical sleeves 20A and 20B at adjacent points. The short 24 is electrically connected between the cylindrical sleeves 20A and 20B at adjacent points on the side of the microdevice 12 opposite the tuning circuit 26A.

Figure 2B:
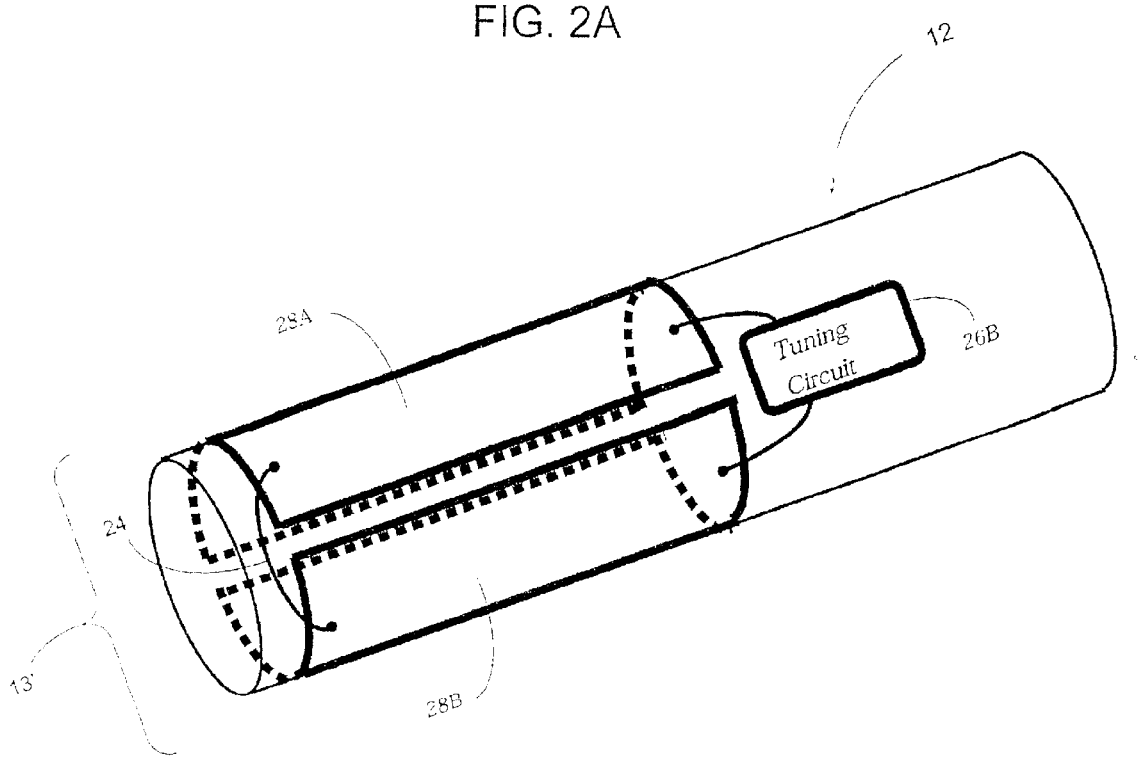
FIG. 2B depicts a second embodiment of a loop antenna located on the case of an implantable microdevice.

An alternative embodiment of a loop antenna 13' is shown in FIG. 2B. In this embodiment, a pair of parallel semi-cylinders 28A and 28B, with concave sides facing each other, on the case of the microdevice 12, form the radiating element of the loop antenna. The edges of the semi-cylinders 28A and 28B are separated by an insulating material or by gaps. The tuning element for the antenna 13' comprises a tuning circuit 26B and a short 24. The tuning circuit 26B is electrically connected between the semi-cylinders 28A and 28B at one end of the semi-cylinders 28A and 28B, and the short 24 is electrically connected between the semi-cylinders 28A and 28B at the opposite end.

The embodiments described in FIGS. 2A and 2B are intended for use with a microdevice having a cylindrical case. Such a cylindrical microdevice is well suited for implanting using a large gauge needle or a cannula. However, those skilled in the art will recognize that many other shapes are viable for implantable microdevices. While the cylindrical and semi-cylindrical radiating elements of FIGS. 2A and 2B may not be appropriate for a non-cylindrical microdevice, the concepts taught for a cylindrical microdevice are readily adaptable to other shapes, and fall within the scope of the present invention.

Figure 3A:
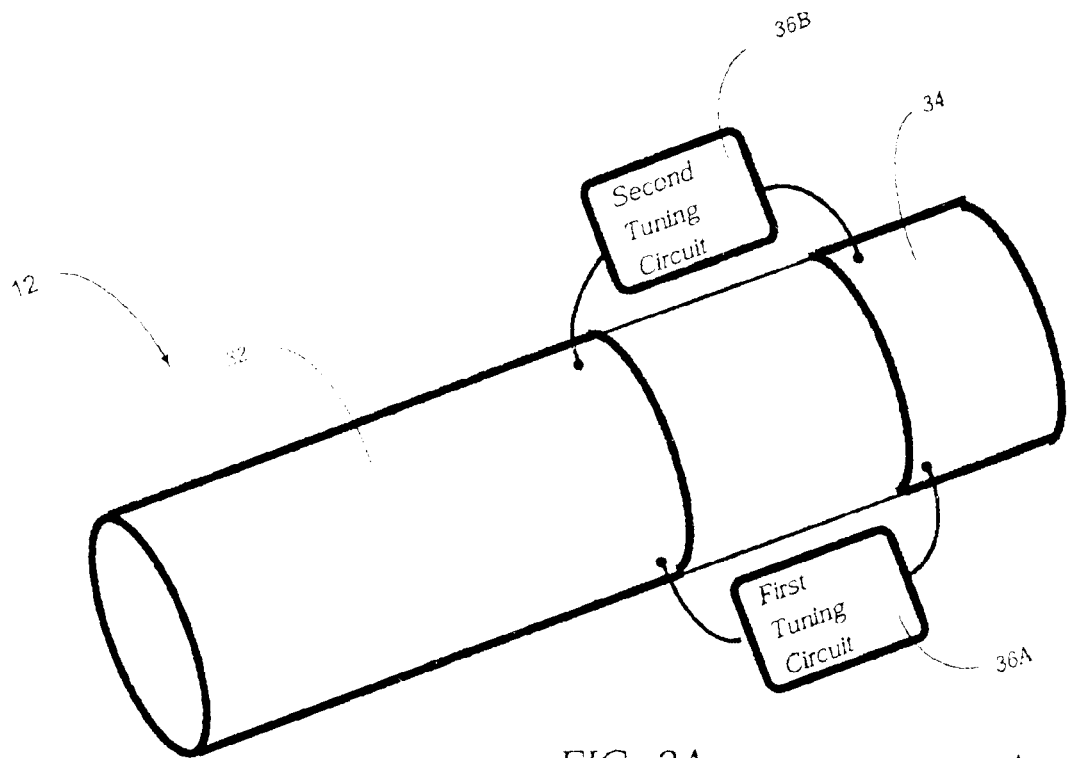
FIG. 3A shows a preferred embodiment of a loop antenna created from the electrodes of a microdevice.

Known microstimulators include electrodes at each end of the microstimulator body. A preferred embodiment of the present invention is shown in FIG. 3A, which uses the existing microstimulator electrodes 32 and 34 as the radiating element of the loop antenna. This embodiment is similar to the embodiment described in FIG. 2A, except that in FIG. 3A, the two cylinders that form the radiating element are not connected by a short. Such a connection would prevent the electrodes from performing their primary task of tissue stimulation. Here, the tuning circuit 26A and short 24 of FIG. 2A are replaced by a first tuning circuit 36A and a second tuning circuit 36B. The first and second tuning circuits 36A and 36B and the electrodes 32 and 34 are designed to provide a resonant circuit at the transmit frequency, but the first and second tuning circuits 36A and 36B also are designed to have high impedance at stimulation frequencies. Thus, the electrodes 32 and 34 may serve both for stimulation and for data transmission.

Figure 3B:
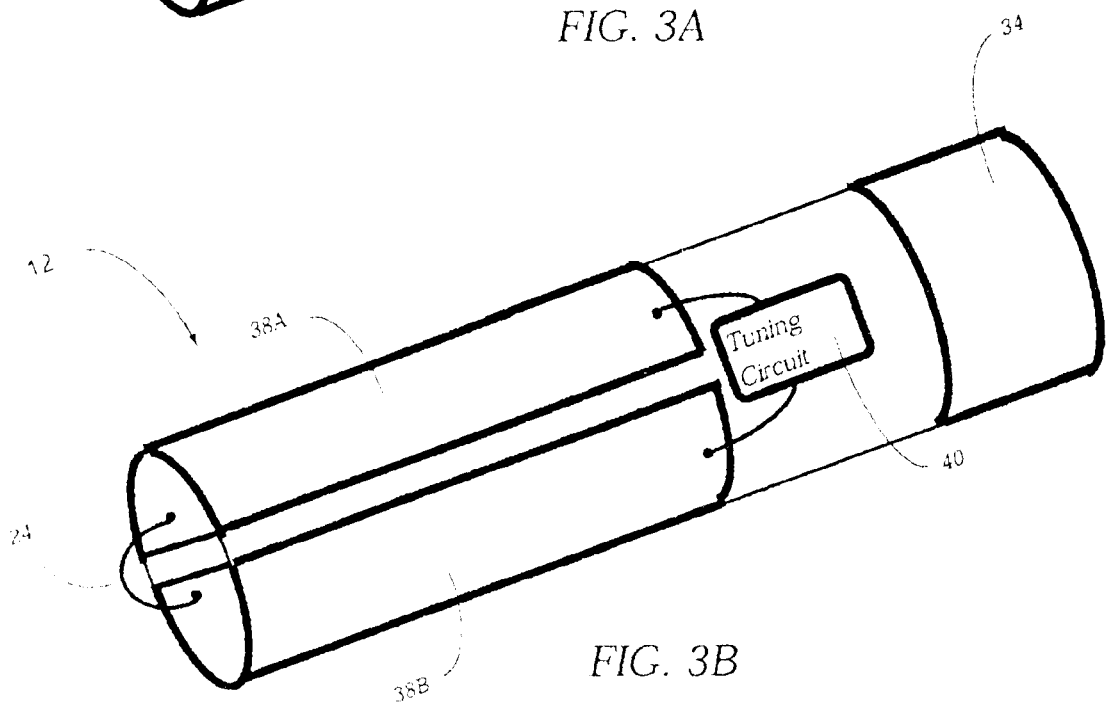
FIG. 3B shows a second preferred embodiment of a loop antenna created from one electrode of a microdevice.

A second embodiment of a loop antenna using a microstimulator electrode as the radiating element is shown in FIG. 3B. In this embodiment, the electrode on one end of the microstimulator is divided by a gap, or an insulator, into two semi-cylindrical halves 38A and 38B. These semi-cylinders 38A and 38B are then electrically connected by a tuning circuit 40 at one end, and a short 24 at the opposite end.

Other electrode arrangements will be apparent to those skilled in the art. Many of these arrangements may be modified to provide a radiating element for a loop antenna, and such arrangements are intended to fall within the scope of the present invention.

The design of a tuning circuit to combine with the radiating elements described by FIGS. 2A, 2B, 3A, and 3B, or other suitable radiating elements, is often difficult because of the difficulty in modeling the electrical behavior of such radiating elements. In the case of a receive circuit, this difficulty may be dealt with by using a tuning circuit comprising an array of capacitors and varactors. The varactors may be adjusted to arrive at the desired resonant circuit needed for efficient operation of the receive circuit.

Figure 4A:
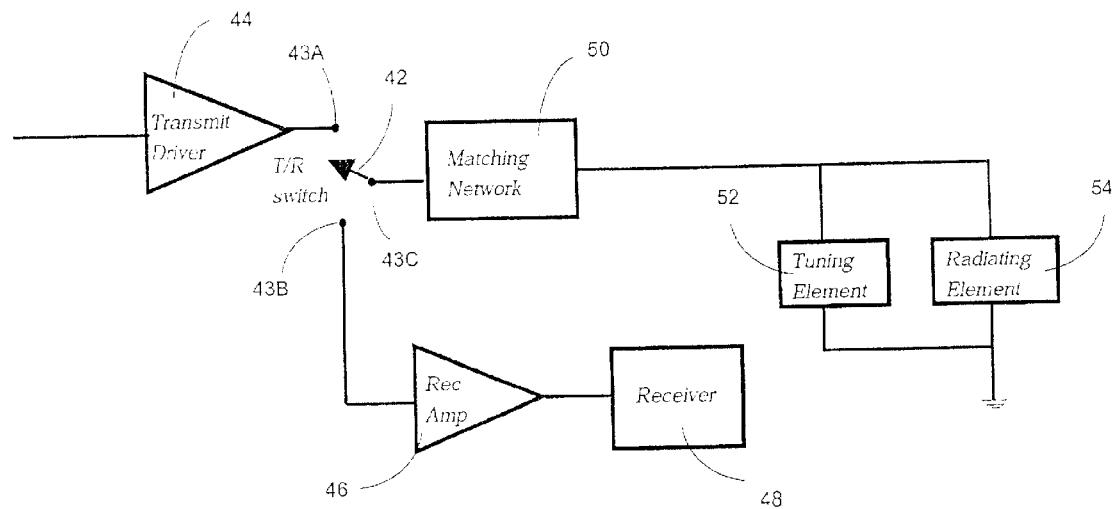
FIG. 4A shows a telemetry system with a parallel connection.

The loop antenna of the present invention may be matched electrically to communication circuits in several ways to create an effective telemetry system. These ways include the use of series and parallel matching circuits. An example of a parallel matching circuit is shown in FIG. 4A. A transmit/receive switch 42 functionally has a first switched contact 43A and a second switched contact 43B, and one fixed contact 43C. A transmit driver 44 is connected to the first switched contact 43A, and a receiver amplifier 46 is connected to the second switched contact 43B. The receiver amplifier 46 amplifies received signals and provides the amplified signal to the receiver 48. The fixed contact 43C of the transmit/receive switch 42 connects to a matching network 50, and the matching network 50 connects to a tuning element 52 and a radiating element 54, which tuning element 52 and radiating element 54 are configured in a parallel relationship.

In operation, the telemetry system of FIG. 4A functions as a transmit circuit by controlling the switch 42 so that the fixed contact 43C is connected to the first switched contact 43A. With the switch 42 in this position, the output of the transmit driver 44 is applied through the matching network 50 to the parallel-configured tuning element 52 and radiating element 54, and is transmitted from the radiating element 54.

When the fixed contact 43C is connected to the receiver amplifier 46, the telemetry system of FIG. 4A functions as a receiving circuit. That is, signals received through the parallel combination of the tuning element 52 and radiating element 54 are applied through the matching network 50 to the receiver amplifier 46. The output of the receiver amplifier 46 is then sent to the receiver 48.

Figure 4B:
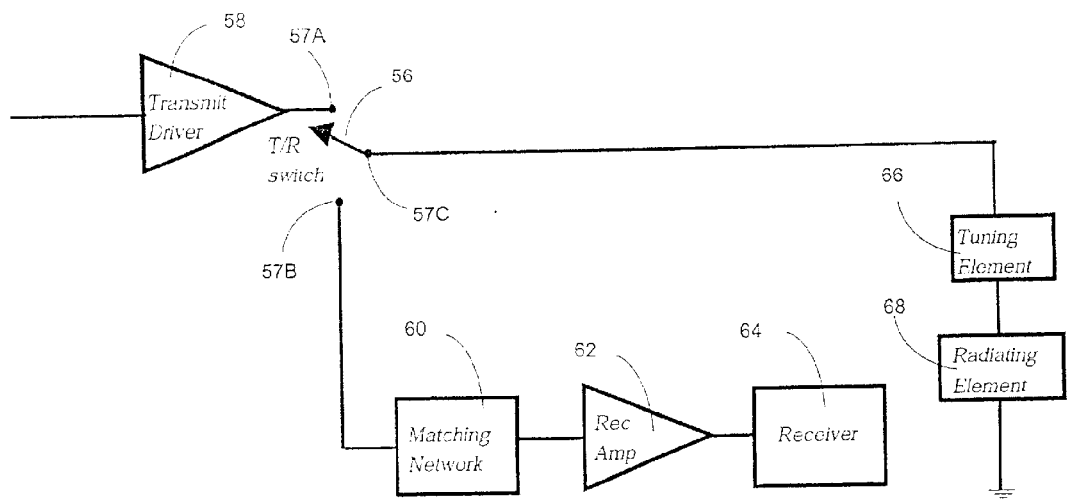
FIG. 4B shows a telemetry system with a series connection.

A telemetry system including a series matching circuit is shown in FIG. 4B. A transmit/receive switch 56 functionally has a first switched contact 57A and a second switched contact 57B, and one fixed contact 57C. A transmit driver 58 is connected to the first switched contact 57A, and a matching network 60 is connected to the second switched contact 57B. The matching network 60 provides received signals to a receiver amplifier 62, and the receiver amplifier 62 provides an amplified signal to a receiver 64. The fixed contact 57C of the transmit/receive switch 56 is connected to a tuning element 66, and the tuning element 66 is connected in series to a radiating element 68.

The telemetry system of FIG. 4B functions operationally as a transmit circuit by controlling the switch 56 so that the fixed contact 57C is connected to the first switched contact 57A. With the switch 56 in this position, the output of the transmit driver 58 is applied to the serial-configured tuning element 66 and radiating element 68, and is transmitted from the radiating element 68.

When the fixed contact 57C is connected to the second switched contact 57B, the telemetry system of FIG. 4B functions as a receiving circuit. That is, signals received through the series combination of the tuning element 66 and radiating element 68 are sent through the matching network 60 to the receiver amplifier 62. The output of the receiver amplifier 62 is then sent to the receiver 64.

Other telemetry systems configurations will be apparent to those skilled in the art. The present invention relates to the use of a radiating element formed on the case of a microdevice, and the examples of telemetry systems shown in FIGS. 4A and 4B are merely provided as particular embodiments of systems within which the invention may be practiced. Any application of a radiating element as described herein, formed on the case of a microdevice, is intended to fall within the scope of the present invention.

While the invention herein disclosed has been described by means of specific embodiments and applications thereof, numerous modifications and variations could be made thereto by those skilled in the art without departing from the scope of the invention set forth in the claims.

What is claimed is:

1. An improved, implantable microdevice configured for sensing and/or affecting a parameter of a patient's body via two or more external electrodes and having a case sized and cylindrically shaped for implantation via injection into the patient's body, wherein said implantable microdevice is configured via communication circuitry within the housing for RF communication with one or more devices external to the microdevice, wherein said improvement comprises a loop antenna formed external to the cylindrically shaped microdevice and said loop antenna comprises:

a radiating element, wherein said radiating element is electrically conducting and formed on the case of the microdevice, wherein said radiating element comprises two spaced apart cylindrical sleeves on the case of the microdevice and wherein said sleeves additionally function as the electrodes of the microdevice for sensing and/or affecting a parameter of the patient's body;

a tuning element electrically connected to said radiating element, wherein said tuning element and said radiating element combine to form a resonant circuit; and wherein said loop antenna is electrically connected to communications circuitry housed within the microdevice to create a telemetry system for the microdevice suitable for operation in the range of 402 MHz to 405 MHz.

2. The loop antenna of claim 1 wherein said tuning element is electrically connected across said two spaced apart cylindrical sleeves.

3. The loop antenna of claim 1 wherein said radiating element comprises two spaced apart semi-cylindrical sleeves on the case of the microdevice and wherein said sleeves additionally function as one of the electrodes of the microdevice for sensing and/or affecting a parameter of the patient's body.

4. The loop antenna of claim 3 wherein said tuning element is electrically connected across said two spaced apart semi-cylindrical sleeves.

5. The loop antenna of claim 1 wherein said telemetry system receives a control signal from an external device.

6. The loop antenna of claim 1 wherein said telemetry system transmits a signal to an external device.

7. The loop antenna of claim 1 wherein said tuning element and said radiating element are electrically connected in a parallel circuit.

8. The loop antenna of claim 1 wherein said tuning element and said radiating element are electrically connected in a serial circuit.

9. The loop antenna of claim 1 wherein said tuning element comprises at least one capacitor.

10. The loop antenna of claim 1 wherein said tuning element comprises at least one varactor.

11. The loop antenna of claim 1 wherein said tuning element comprises at least one capacitor and at least one varactor.

12. The loop antenna of claim 1 wherein the microdevice is a microstimulator and the electrodes are used for stimulating tissue in the patient's body.

13. The loop antenna of claim 1 wherein the microdevice is a microsensor and the electrodes are used for sensing a parameter of the patient's body.

14. A telemetry system for transmitting signals from an implantable microdevice configured for sensing and/or affecting a parameter of a patient's body via two or more external electrodes and having a case sized and cylindrically shaped for implantation via injection into the patient's body, wherein said implantable microdevice is configured via circuitry within the housing for RF communication with one or more devices external to the microdevice, said telemetry system comprising:

a transmit driver including a transmit driver output;

a matching network with a first connection and a second connection, wherein said first connection of said matching network is connected to said transmit driver output;

a tuning element; and a radiating element formed on the case of the microdevice, wherein said radiating element electrically behaves as a loop antenna, and wherein said tuning element and said radiating element are connected in a parallel circuit, wherein said parallel circuit has a first connection and a second connection, and wherein said second connection of said matching network is connected to said first connection of said parallel circuit, and wherein said second connection of said parallel circuit is connected to ground.

15. The telemetry system of claim 14 wherein the microdevice is a microstimulator configurable for stimulating tissue in the patient's body.

16. The telemetry system of claim 14 wherein said tuning element comprises at least one capacitor.

17. The telemetry system of claim 14 wherein the operating frequency of said telemetry system is in the range of 402 to 405 MHz.

18. The telemetry system of claim 14 wherein said telemetry system additionally includes the capability of receiving signals, and wherein said telemetry system further comprises:

a receiver amplifier with an input and an output;

a receiver with an input, wherein said output of said receiver amplifier is connected to said input of said receiver;

a transmit/receive switch including a first switched connection, a second switched connection, and a fixed connection;

wherein said transmit/receive switch is switchably connected between said transmit driver and said matching network, wherein said output of said transmit driver is connected to said first switched connection, and wherein said fixed connection is connected to said first connection of said matching network; and wherein said receiver amplifier input is switchably connected to said second switched connection of said transmit/receive switch.

19. The telemetry system of claim 18 wherein said tuning element comprises at least one varactor.

20. A telemetry system for receiving signals for an implantable microdevice configured for sensing and/or affecting a parameter of a patient's body via two or more external electrodes and having a case sized and cylindrically shaped for implantation via injection into the patient's body, wherein said implantable microdevice is configured via circuitry within the housing for RF communication with one or more devices external to the microdevice, said telemetry system comprising:

a receiver with an input;

a receiver amplifier with an input and an output, wherein said output of said receiver amplifier is connected to said input of said receiver;

a matching network with a first connection and a second connection, wherein said first connection of said matching network is connected to said input of said receiver amplifier;

a tuning element;

a radiating element formed on the case of the microdevice, wherein said radiating element electrically behaves as a loop antenna; and wherein said tuning element and said radiating element are connected in a parallel circuit, wherein said parallel circuit has a first connection and a second connection, and wherein said second connection of said matching network is connected to said first connection of said parallel circuit, and wherein said second connection of said parallel circuit is connected to ground.

21. The telemetry system of claim 20 wherein the microdevice is a microstimulator configurable for stimulating tissue in the patient's body.

22. The telemetry system of claim 20 wherein said tuning element comprises at least one capacitor.

23. The telemetry system of claim 20 wherein said tuning element comprises at least one varactor.

24. The telemetry system of claim 20 wherein said tuning element comprises at least one capacitor and at least one varactor.

25. The telemetry system of claim 20 wherein the operating frequency of said telemetry system is in the range of 402 to 405 MHz.

26. The telemetry system of claim 20 wherein said telemetry system includes the capability of transmitting signals, and wherein said telemetry system further comprises:

a transmit driver with an output;

a transmit/receive switch including a first switched connection, a second switched connection, and a fixed connection;

wherein said transmit/receive switch is switchably connected between said receiver amplifier and said matching network, wherein said first connection of said matching network is connected to said fixed connection, and wherein said second switched connection is connected to said receiver amplifier; and wherein said output of said transmit driver is connected to said first switched connection.

27. A telemetry system for transmitting signals from an implantable microdevice configured for sensing and/or affecting a parameter of a patient's body via two or more external electrodes and having a case sized and cylindrically shaped for implantation via injection into the patient's body, wherein said implantable microdevice is configured via circuitry within the housing for RF communication with one or more devices external to the microdevice, said telemetry system comprising:

a transmit driver with an output;

a tuning element with a first connection and a second connection, wherein said first connection of said tuning element is connected to said output of said transmit driver;

a radiating element with a first connection and a second connection, wherein said radiating element is formed on the case of the microdevice, and wherein said radiating element electrically behaves as a loop antenna, wherein said first connection of said radiating element is connected to said second connection of said tuning element, and wherein said second connection of said radiating element is connected to ground;

a matching network with an input and an output;

a receiver amplifier with an input and an output, wherein said output of said matching network is connected to said input of said receiver amplifier;

a receiver with an input, wherein said output of said receiver amplifier in connected to said input of said receiver;

a transmit/receive switch including a first switched connection, a second switched connection, and a fixed connection;

wherein said transmit/receive switch is switchably connected between said transmit driver and said tuning element, wherein said output of said transmit driver is connected to said first switched connection, and wherein said fixed connection is connected to said first connection of said tuning element; and wherein said input of said matching network is connected to said second switched connection of said transmit/receive switch.

28. The telemetry system of claim 27 wherein said tuning element comprises at least one varactor.

29. The telemetry system of claim 27 wherein the microdevice is a microstimulator configurable for stimulating tissue in the patient's body.

30. The telemetry system of claim 27 wherein said tuning element comprises at least one capacitor.

31. The telemetry system of claim 27 wherein the operating frequency of said telemetry system is in the range of 402 to 405 MHz.

32. A telemetry system for receiving signals for an implantable microdevice configured for sensing and/or affecting a parameter of a patient's body via two or more external electrodes and having a case sized and cylindrically shaped for implantation via injection into the patient's body, wherein said implantable microdevice is configured via circuitry within the housing for RF communication with one or more devices external to the microdevice, said telemetry system comprising:

a matching network with an input and an output;

a receiver amplifier with an input and an output, wherein said receiver amplifier input is connected to said output of said matching network;

a receiver with an input, wherein said output of said receiver amplifier is connected to said input of said receiver;

a tuning element with a first connection and a second connection, wherein said first connection of said tuning element is connected to said input of said matching network;

a radiating element with a first connection and a second connection, wherein said radiating element is formed on the case of the microdevice, and wherein said radiating element electrically behaves as a loop antenna; and wherein said first connection of said radiating element is connected to said second connection of said tuning element, and wherein said second connection of said radiating element is connected to ground.

33. The telemetry system of claim 32 wherein the microdevice is a microstimulator configurable for stimulating tissue in the patient's body.

34. The telemetry system of claim 32 wherein said tuning element comprises at least one capacitor.

35. The telemetry system of claim 32 wherein said tuning element comprises at least one varactor.

36. The telemetry system of claim 32 wherein said tuning element comprises at least one capacitor and at least one varactor.

37. The telemetry system of claim 32 wherein the operating frequency of said telemetry system is in the range of 402 to 405 MHz.

38. The telemetry system of claim 32 wherein said telemetry system includes the capability of transmitting signals, and wherein said telemetry system further comprises:

a transmit driver with an output;

a transmit/receive switch including a first switched connection, a second switched connection, and a fixed connection;

wherein transmit/receive switch is switchably connected between said tuning element and said matching network, wherein said input of said matching network is connected to said second switched connection, and wherein said fixed connection is connected to said first connection of said tuning element; and wherein said output of said transmit driver is connected to said first switched connection.

* * * * *